United States Patent
Massaro et al.

(10) Patent No.: US 10,178,857 B2
(45) Date of Patent: Jan. 15, 2019

(54) INSECT SINGULATOR SYSTEM

(71) Applicant: Verily Life Sciences LLC, Mountain View, CA (US)

(72) Inventors: Peter Massaro, Belmont, CA (US); Victor Criswell, Mountain View, CA (US); Martin Sheridan, Redwood City, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 168 days.

(21) Appl. No.: 15/412,169

(22) Filed: Jan. 23, 2017

(65) Prior Publication Data

US 2018/0206473 A1   Jul. 26, 2018

(51) Int. Cl.
| | |
|---|---|
| A01K 67/033 | (2006.01) |
| A01M 1/06 | (2006.01) |
| A01M 1/02 | (2006.01) |
| A01K 29/00 | (2006.01) |
| A01M 1/10 | (2006.01) |
| A01M 29/12 | (2011.01) |
| A01M 29/34 | (2011.01) |
| G06T 7/00 | (2017.01) |

(52) U.S. Cl.
CPC ........... *A01M 1/026* (2013.01); *A01K 29/005* (2013.01); *A01K 67/0339* (2013.01); *A01M 1/103* (2013.01); *A01M 1/106* (2013.01); *A01M 29/12* (2013.01); *A01M 29/34* (2013.01); *G06T 7/0002* (2013.01); *G06T 2207/10004* (2013.01)

(58) Field of Classification Search
CPC ....... A01K 67/033; A01M 1/026; A01M 1/06; A01M 1/106; A01M 2200/012

USPC .................................. 119/6.5, 6.7; 43/107
See application file for complete search history.

(56) References Cited

U.S. PATENT DOCUMENTS

| | | | |
|---|---|---|---|
| 3,874,335 A | | 4/1975 | Galasso |
| 4,794,724 A | * | 1/1989 | Peters ................. A01M 1/02 43/107 |
| 5,406,743 A | * | 4/1995 | McSherry ............. A01M 1/02 43/107 |
| 5,575,236 A | * | 11/1996 | Pogue ................. A01K 67/033 119/250 |

(Continued)

FOREIGN PATENT DOCUMENTS

WO        2016093673        6/2016

OTHER PUBLICATIONS

International Application No. PCT/US2018/013953, "International Search Report and Written Opinion", Apr. 4, 2018, 12 pages.

*Primary Examiner* — Yvonne R Abbott-Lewis
(74) *Attorney, Agent, or Firm* — Kilpatrick Townsend & Stockton LLP (57) ABSTRACT

In one aspect, a singulation chamber apparatus defines a volume having a receiving end and an opposing end. The receiving end may be couplable to an insect chamber for a plurality of ambulatory insects and define an opening to receive the plurality of ambulatory insects from the insect chamber. A surface of the chamber is ramped to provide a pathway between the receiving end and the opposing end such that the opposing end is elevated with respect to the first end via the ramped surface. The pathway has a width sized to accommodate a single-file line of the plurality of ambulatory insects traversing the ramped surface.

36 Claims, 6 Drawing Sheets

(56) References Cited

U.S. PATENT DOCUMENTS

| | | | |
|---|---|---|---|
| 6,655,079 B1 * | 12/2003 | Bernard | A01M 1/2005 |
| | | | 43/107 |
| 7,632,167 B1 * | 12/2009 | Miller | A01M 1/106 |
| | | | 43/121 |
| 8,025,027 B1 | 9/2011 | Morales-Ramos et al. | |
| 8,667,731 B2 | 3/2014 | Panella et al. | |
| 2005/0103276 A1 * | 5/2005 | Davis | A01K 1/0613 |
| | | | 119/6.5 |
| 2009/0126257 A1 * | 5/2009 | Banfield | A01M 1/106 |
| | | | 43/121 |
| 2013/0081572 A1 | 4/2013 | Chen et al. | |
| 2013/0293710 A1 | 11/2013 | Afanasyev et al. | |
| 2017/0042131 A1 * | 2/2017 | Unger | A01K 67/033 |
| 2017/0273291 A1 | 9/2017 | Yoo et al. | |

* cited by examiner

INSECT SINGULATOR SYSTEM

TECHNICAL FIELD

The present disclosure generally relates to insect singulator systems, and, more particularly, although not necessarily exclusively, to systems for causing insects to self-separate for individual insect analysis.

BACKGROUND

Facilities raise insects for research, testing, and other scientific purposes. Once the insects reach certain developmental stages, such facilities may wish to categorize the insects based on common characteristics (e.g., gender, size, fitness, etc.) For example, various techniques for the control of mosquito populations involve the generation of sterile male insects for release into the wild for mating with local females. Such techniques were developed as a solution for populations suffering from mosquito-vectored diseases. As part of this development, it is important to assess the relative fitness of the male mosquitoes raised in the facility and their ability to compete with the local wild male population.

Sensors and other devices may be used to access the characteristics of mosquitoes and other insects raised in a facility for sorting the insects into categories However, the presence of a large quantity of insects can prevent the sensors from analyzing the insects individually and determining an appropriate category for each insect. Similarly, physically separating the insects by category can be extremely difficult.

SUMMARY

In some aspects of the present disclosure, a system may include a singulation chamber for an insect singulator system that is usable to separate a group of insects using non-forcible means to analyze the characteristics of the insects and sort them based on the characteristics.

In one aspect, an apparatus, includes a chamber defining a volume having a receiving end and an opposing end, wherein the receiving end is couplable to an insect chamber for a plurality of ambulatory insects and defines an opening to receive the plurality of ambulatory insects from the insect chamber, and wherein a surface of the chamber is ramped to provide a pathway between the receiving end and the opposing end such that the opposing end is elevated with respect to the first end via the ramped surface, the pathway having a width sized to accommodate a single-file line of the plurality of ambulatory insects traversing the ramped surface.

In another aspect a system includes an insect chamber including a plurality of ambulatory insects, an imaging platform positioned proximate to an imaging device configured to generate a visual medium including an insect of the plurality of ambulatory insects, the visual medium usable to sort the insect into a new chamber based on a characteristic of the insect captured in the visual medium, and a singulation chamber defining a volume having a receiving end coupled to the insect chamber and an opposing end coupled to the imaging platform, the receiving end defining an opening to receive the plurality of ambulatory insects, wherein a surface of the singulation chamber is ramped to provide a pathway between the opening and the imaging platform such that the imaging platform is elevated with respect to the opening via the ramped surface, the pathway having a width sized to accommodate a single-file line of the plurality of ambulatory insects traversing the ramped surface.

In another aspect, a method includes (i) providing a singulation chamber, the singulation chamber defining a volume having a receiving end coupled to the insect chamber and an opposing end, the receiving end defining an opening, wherein a surface of the singulation chamber is ramped to provide a pathway between the receiving end and the opposing end such that the opposing end is elevated with respect to the opening via the ramped surface, the pathway having a width sized to accommodate a single-file line of a plurality of ambulatory insects traversing the ramped surface, (ii) positioning an insect chamber including the plurality of ambulatory insects at the receiving end of the singulation chamber to allow the plurality of ambulatory insects to enter the singulation chamber from the insect chamber through the opening, and (iii) receiving an insect of the plurality of ambulatory insects at the opposing end, the insect having voluntarily navigated the pathway in a single-file line comprising a subset of the plurality of ambulatory insects.

In a further aspect, an apparatus includes a chamber defining a volume having a plurality of receiving ends and a common opposing end, wherein the plurality of receiving ends are couplable to a plurality of insect chambers, each insect chamber of the plurality of insect chambers including a corresponding set of ambulatory insects, each receiving end of the plurality of receiving ends defining a respective opening to receive the corresponding set of ambulatory insects, and wherein a surface of the chamber is ramped to provide a plurality of pathways between the plurality of receiving ends and the common opposing end such that the common opposing end is elevated with respect to the plurality of receiving ends, each pathway of the plurality of pathways having width size to accommodate a single-file line of the corresponding set of ambulatory insects traversing each pathway.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of singulator systems and methods for ambulatory insects. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of an Insect Singulation Chamber

A commercial rearing program may raise modified insects for use in controlling a local insect population. For example, a rearing program may engineer male mosquitoes with desirable traits, such as sterility (e.g., lacking the ability to produce viable offspring) and fitness levels to compete with wild-type insects of the same species. As the modifications are gender-specific, a population of reared mosquitoes is sorted to separate the female mosquitoes from the male mosquitoes. A sensor, camera, or other suitable means may be used to determine the sex of the mosquitoes in the population based on physical characteristics of the mosquito (e.g., shape, size, etc.). A system may include a singulation chamber having specified geometries (e.g., width, height) and features (ramped surfaces) that encourage mosquitoes to voluntarily navigate through the singulation chamber in a single-file manner to be sorted based on their physical characteristics.

Figure 1:
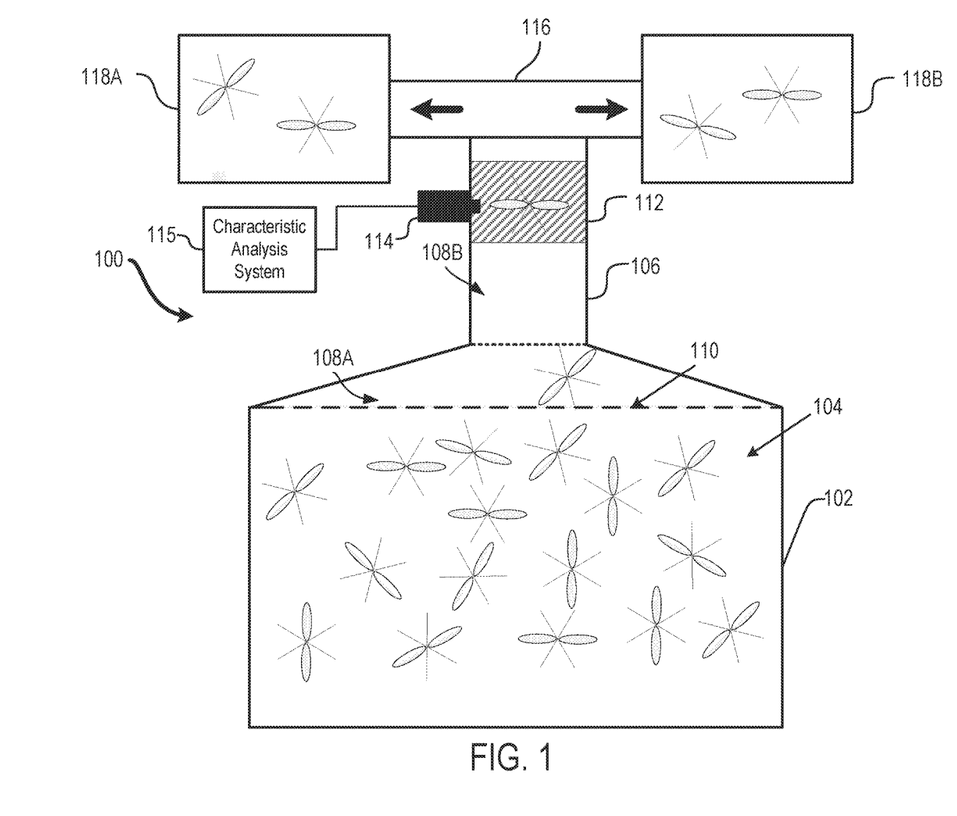
FIG. 1 is a top cross-sectional view of an insect singulator system according to some aspects of the present disclosure.

One illustrative aspect of the present disclosure comprises an insect singulator system 100 as shown in FIG. 1. As used herein, the terms "singulate," "singulator," and "singulation" refer to a device, process, or other means for separating a set of insects into individual insects by creating a measurable gap between each insect to allow proper analysis and sortation of each insect in the group. The insect singulator system 100 includes an insect chamber 102 including a group of mosquitoes 104. The mosquitoes 104 are ambulatory insects that have reached a developmental stage in which they are capable of walking or crawling. The insect chamber 102 is an enclosed chamber and may comprise any suitable material for containing live mosquitoes (e.g., mesh, plastic, glass, etc.).

The insect chamber 102 is connected to a singulation chamber 106. The singulation chamber 106 includes a receiving end 108A and an opposing end 108B. The receiving end 108A of the singulation chamber 106 is coupled to a side of the insect chamber 102 includes an opening 110 for allowing the mosquitoes 104 to enter the singulation chamber 106. As described in further detail herein, the singulation chamber 106 is configured to encourage the mosquitoes to individually navigate from the insect chamber 102, through the opening 110, and into the receiving end 108A to traverse a pathway toward the opposing end 1086 without exerting any physical force on the mosquitoes 104. The specific dimensions of the opening 110 may be dependent on the average size of the mosquitoes positioned in the insect chamber 102. For example, the opening 110 may be large enough for a mosquito to fly or walk into the opening, but small enough to one allow one or two mosquitoes to pass through the opening at the same time. In one illustrative example, the mosquitoes have heights between 1.4 millimeter and 2.3 millimeters and widths (e.g., leg span or wingspan) between 1.9 millimeters and 2.7 millimeters, with the typical average height of the mosquitoes being 1.8 millimeters and the average width being 2.4 millimeters. The opening 110 of the singulation chamber 106 includes a maximum height or width (or diameter) of approximately 2.7 millimeters to allow the mosquitoes to easily crawl or fly through the opening 110, but remain small enough to only allow a single mosquito through at a time. The pathway between the receiving end 108A and the opposing end 108B and defined by a surface of the chamber 106 is wide enough to allow the mosquitoes 104 to navigate through at least a portion of the chamber 106 only in a single-file manner. A portion of the chamber 106 may have a height that prevents the mosquitoes 104 from flying, requiring them to navigate the pathway by walking, or crawling. Still further, as discussed in detail herein, the singulation chamber 106 optionally includes features, such as ramps that are positioned to orient the mosquitoes 104 such that they navigate the pathway headfirst toward an imaging platform 112. For example, some insects may exhibit a preference for travelling from lower to higher ground. Thus, providing a ramped surface may encourage the insects to travel up the ramp along or towards the pathway.

In this example, the imaging platform 112 is positioned at an end of the opposing end 108B, opposite the end connected to the receiving end 108A. The imaging platform 112 corresponds to a location at which the mosquitoes 104 are analyzed and sorted based on their observed characteristics. In some aspects, the imaging platform 112 is positioned within the chamber 106. In other aspects, the imaging platform 112 is connected to the chamber 106 at the opposing end 108B. An imaging device 114 is positioned proximate to the imaging platform 112 to analyze a mosquito located on the imaging platform 112. Non-limiting examples of the imaging device 114 include one or more of a camera, a microphone, and a sensor that uses ultrasonic Doppler monitoring of the mosquito's movement (e.g., wing movement).

The imaging device 114 is connected to a characteristic analysis system 115. In some aspects, the imaging device 114 is configured to generate an image, video, waveform, or other visual medium that captures a characteristic of the mosquito. The imaging device 114 transmits the medium to the characteristic analysis system 115, which determines how to classify the mosquito based on the characteristic. In some aspects, the characteristic analysis system 115 includes a processor and a memory. The processor may execute algorithms or a machine-learning system, such as a neural network, to analyze the medium generated by the imaging device 114. For example, the characteristic analysis system 115 may include an algorithm stored in memory that is executable by a processor to identify visual objects (e.g., mosquitos) within a visual medium and label the object according to a class associated with the object (e.g., male mosquito vs. female mosquito). In additional and alternative examples, the characteristic analysis system 115 may also include display unit for manually classifying or confirming a classification of each mosquito 104 positioned on the imaging platform 112 based on an observed characteristic(s) (e.g., male characteristics).

A sorting device 116 positioned proximate to the imaging platform 112 is configured to sort the mosquitoes 104 into an appropriate sorting chamber 118A, 118B based on whether or not the desired characteristic is present. For example, in response to determining that a mosquito 104 positioned on the imaging platform 112 has characteristics consistent with a male mosquito, the sorting device 116 may direct or otherwise force the mosquito 104 into sorting chamber 118A. Similarly, in response to determining that the mosquito 104 does not have characteristics consistent with a male mosquito, the sorting device 116 may force the mosquito 104 into sorting chamber 118B.

A singulation chamber according to aspects of the present disclosure allows mosquitoes, or other ambulatory insects, to singulate themselves without the use of force. For example, conventional systems for separating and sorting insects may forcibly separate the insects from each other to allow an imaging device 114 to analyze them for the desired characteristics. Forced singulation of the insects may cause damage or injury that may undermine the objectives of the sortation. For example, non-voluntary manipulation of an insect may cause aggressive behavior that prevents characteristics such as fitness levels or natural behavior from being observed. Further, such aggressive behavior may cause the insects to injure themselves, injure other insects in the insect chamber 102 or the sorting chambers 118A, 118B, or exhibit behavior resistive to the forced singulation. Similarly, the device or other means for applying the force may injure the insect (e.g., severing a limb, antennae, or wing of the insect, disorienting the insect, damaging an eye or other sensory element of the insect). Accordingly, a system configured to encourage the insects to self-singulate as they navigate toward an imaging device for sorting yields healthier mosquitoes for serving the purposes of the sortation.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure. The various figures described below depict examples of implementations for the present disclosure, but should not be used to limit the present disclosure.

Various aspects of the present disclosure may be implemented for self-singulation and sortation of various types of ambulatory insects. For illustrative purposes, the descriptions herein are directed to mosquitoes, though the descriptions are not intended to be limiting in nature.

Figure 2A:
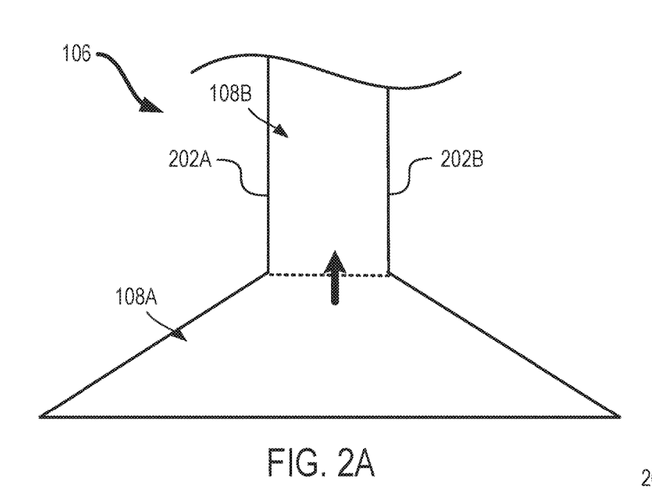
FIG. 2A is a top cross-sectional view of a singulation chamber of the insect singulator system of FIG. 1 according to some aspects of the present disclosure.
Figure 2B:
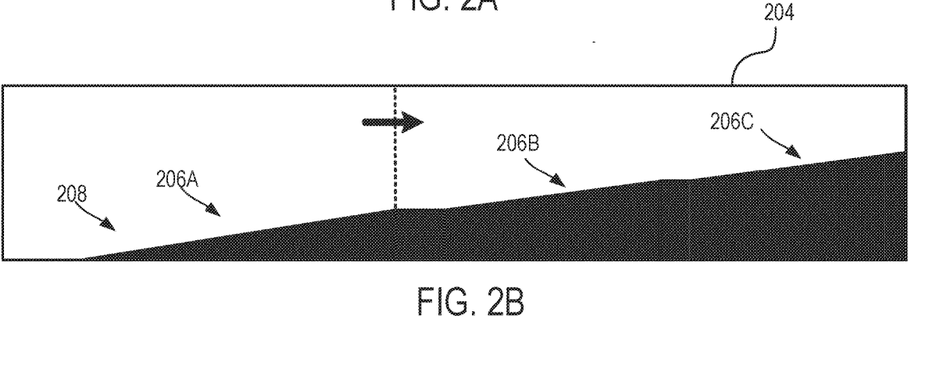
FIG. 2B is a side cross-sectional view of the singulation chamber of FIG. 2A according to some aspects of the present disclosure.

FIGS. 2A-2B examples of show various perspectives of the singulation chamber 106 of FIG. 1. FIG. 2A shows a top view of the singulation chamber 106 and FIG. 2B shows a side view of the singulation chamber 106. The bolded arrows in each figure indicate a consistent orientation of singulation chamber 106 for each perspective and are pointed in the direction of a desired navigation path through the singulation chamber 106.

The receiving end 108A has a funnel-like shape that decreases in width from the portion of the receiving end 108A that is connected to the insect chamber 102 of FIG. 1 toward the opposing end 108B. The opposing end 108B includes a cross-sectional shape of a rectangle. Although a funnel-like shape and a rectangular shape are shown in FIG. 2A for the singulation chamber 106, the singulation chamber 106 may include additional or alternative cross-sectional shapes without departing from the scope of the present disclosure.

The pathway between the receiving end 108A and the opposing end 108B includes a narrow through-bore that allows mosquitoes to navigate through at least a portion of the pathway only in a single-file manner (e.g., one mosquito behind another). In some aspects, the height of the pathway prevents the mosquitoes in the pathway from flying. For example, the height of the pathway may be slightly taller than the mosquitoes. The width of the pathway is sized to prevent the mosquitoes in the pathway from turning around back toward the insect chamber 102 of FIG. 1, or otherwise wandering away from the desired direction toward the imaging platform 112 of FIG. 1. For example, the width of the pathway may be slightly wider than the leg span of the mosquitoes. Returning to the illustrative example wherein the mosquitoes have heights between 1.4 millimeter and 2.3 millimeters and widths between 1.9 millimeters and 2.7 millimeters, the height and width of the pathway may be 2.4 millimeters and 2.8 millimeters, respectively. In other examples, the pathway may be less than 150% taller and wider than the largest mosquito in the insect chamber 102 of FIG. 1.

The singulation chamber 106 includes side walls 202A, 202B extending the length of the singulation chamber 106 from the receiving end 108A to the opposing end 108B. In some aspects, the side walls 202A, 202B of the singulation chamber 106 have a smooth surface. Some insects, such as mosquitoes are resistant from walking or crawling on smooth surfaces. Thus, the smooth surfaces discourage the mosquitoes from walking or crawling on the side walls 202A, 202B of the singulation chamber 106. Similarly, a top 204 of the singulation chamber 106 includes a smooth surface, discouraging the mosquitoes from walking or crawling on any surface other than the bottom or floor of the singulation chamber 106. In some aspects, the smooth surface may include a glass or plastic material. In additional and alternative aspects, the material may be translucent to allow light to be transmitted from outside of the singulation chamber 106 into the singulation chamber 106. In such aspects, a light may be positioned proximate to the opening 110 or a portion of the pathway. Mosquitoes are attracted to the glow of a light, particularly within a dark space. Thus, the position of the light may encourage the mosquitoes to navigate toward the opening 110 or the opposing end 108B.

In some aspects, the surfaces of the singulation chamber 106 may have one or more colors. The colors of the singulation chamber 106 may encourage or discourage the mosquitoes from navigating in the desired direction. Mosquitoes are attracted to light colored surfaces. Accordingly, in some aspects, all or a portion of the singulation chamber 106 may be white or another light color (e.g., light blue, light yellow, etc.) to encourage the mosquitoes to navigate through the opening 110 from the insect chamber 102 of FIG. 1. In additional and alternative aspects, the pathway closer to the opposing end 108B may include a lighter color than pathway closer to the receiving end 108A to encourage the mosquitoes to navigate through the pathway toward the imaging platform 112.

In some aspects, the singulation chamber 106 includes ramps 206A, 206B, 206C. The ramps 206A, 206B, 206C are angled to have an upward incline as the mosquitoes navigate in the desired direction away from opening 110. Mosquitos have natural tendencies to walk in an upward direction on an incline, so the incline of the ramps 206A, 206B, 206C may encourage the mosquitoes to move in the desired direction toward the imaging platform 112 of FIG. 1. Although the ramps 206A, 206B, 206C are shown in both the receiving end 108A and the opposing end 1086 of the singulation chamber 106, one or more of the ramps 206A, 206B, 206C may be positioned in different locations without departing from the scope of the present disclosure. For example, the floor or bottom of the receiving end 108A may not include a ramped surface, while the floor of the opposing end 108B may include the ramps 206B, 206C. In another example, the singulation chamber 106 may include one or two ramps or more than three ramps. In further aspects, the ramps 206A, 206B, 206C may be position on various surfaces of the singulation chamber 106. For example, a portion of the ramp's 206B surface may originate on the side wall 202A of the singulation chamber 106 and a portion of the ramp's 206C surface may originate on the side wall 202B of the singulation chamber 106. Each of the ramps 206B, 206C may terminate on the bottom surface of the singulation chamber's 106 pathway. The orientation of the ramps 206B, 206C may orient the mosquitoes entering the singulation chamber 106 such that they navigate headfirst through the pathway in the desired direction.

Figure 3:
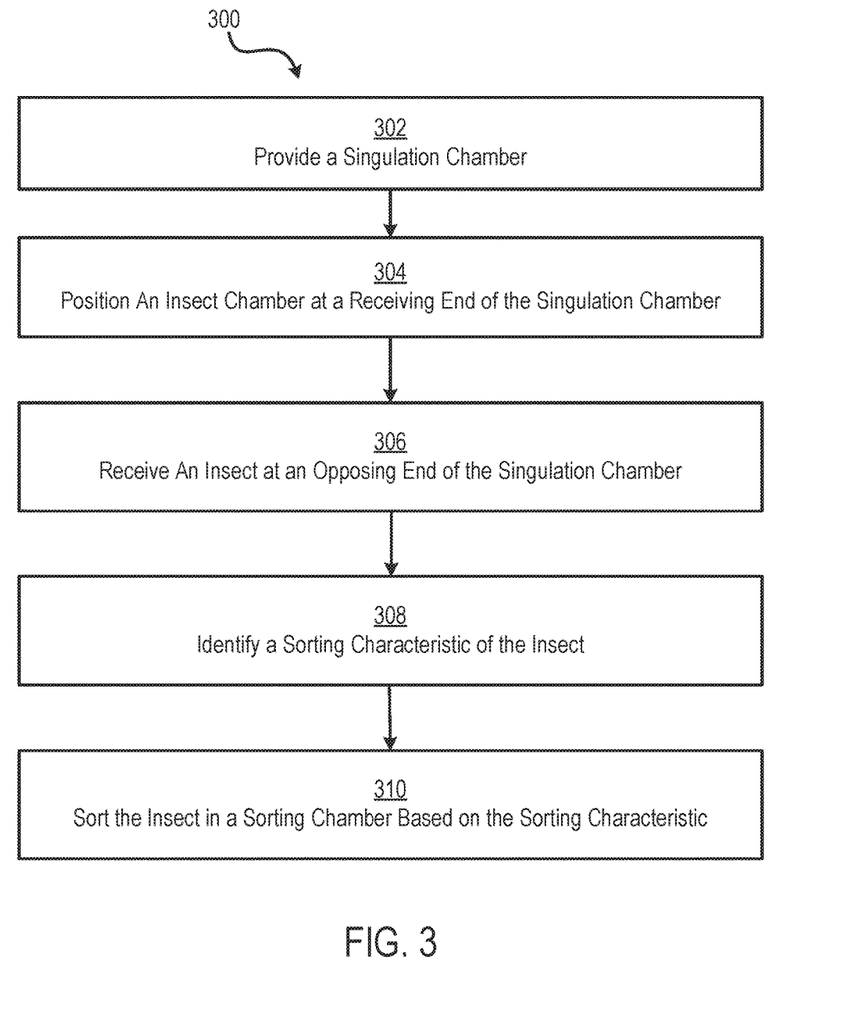
FIG. 3 is a flow chart of a process for sorting insects using a singulation chamber according to some aspects of the present disclosure.

FIG. 3 is a flowchart of a process 300 for sorting insects using a singulation chamber 106. The process is described with respect to the singulation chamber 106 of FIGS. 1-2 and the insect singulator system 100 of FIG. 1, though other implementations are possible without departing from the present disclosure. In some aspects, one or more of the steps shown in FIG. 3 may be shown in a different order. Alternatively, in some aspects, one or more of the steps may be skipped, or additional steps not shown in FIG. 3 may be performed.

The process 300 begins at block 302 when the singulation chamber 106 is provided. As described above, the singulation chamber 106 includes a receiving end 108A and an opposing end 108B. In block 304, the insect chamber 102 having a population of a type of insects, e.g., *Aedes aegypti* mosquitos, is positioned at the receiving end 108A of the singulation chamber 106. The singulation chamber 106 and the insect chamber 102 may be aligned at the opening 110 in both chambers that allows the mosquitoes 104 positioned in the insect chamber 102 to navigate (e.g., walk or fly) through the opening 110 into the singulation chamber 106.

In block 306, an insect (e.g., one of the mosquitoes 104) is received at the opposing end 108B. The geometry and features of the singulation chamber 106 may encourage the insect to navigate itself through the opening 110 into and through the singulation chamber 106 toward the imaging platform 112 positioned at the opposing end 108B of the singulation chamber 106. In some aspects, the singulation chamber 106 includes one or a combination of the geometry and features described herein. In additional and alternative aspects, one or both of the insect chamber 102 and the singulation chamber 106 may include one or more additional features to encourage the insects to self-navigate through the singulation chamber 106 toward the imaging platform 112.

In block 308, a sorting characteristic of the insect is identified. For example, the imaging platform 112 is positioned at the opposing end 108B of the singulation chamber described in block 306. An imaging device 114 may be trained on the imaging platform 112 to capture one or more characteristics of a mosquito located on the imaging platform 112 and transmit a medium including the characteristics to the characteristic analysis system 115 to determine which sorting chamber 118A the sorting device 116 should place the mosquito. Non-limiting examples of sorting characteristics include body shape, the presence or absence of certain body parts, and activity or movement. In one example, the imaging device 114 may be used to distinguish male mosquitoes from female mosquitoes. One characteristic that may be used to distinguish between genders is the mosquito's proboscis, a long, needle-like antenna that extends from the area of its mouth. Male mosquitoes have a feather-like proboscis, while female mosquitoes have a relatively smooth proboscis. The imaging device 114 may include a camera configured to capture an image of the mosquitoes mouth-part and transmit the image to the characteristic analysis system. The characteristic analysis system 115 may include a neural network trained to identify the mouth-part in the image and determine whether the proboscis corresponds to a male or female mosquito.

In block 310, the insect is sorted in a sorting chamber 118A, 118B based on the characteristic determined in block 308. The sorting device 116 may be used to sort the insects into the appropriate sorting chamber 118A, 118B. In some aspects, the characteristic analysis system 115 may control an actuation mechanism configured to actuate the sorting device upon determining whether a characteristic is present in an insect positioned on the imaging platform 112. In one example, the sorting device 116 may include an air machine configured to generate a puff of air that guides the insect toward the sorting chamber 118A, 118B corresponding to the determined characteristic. In another example, the sorting device 116 may include the imaging platform 112 positioned on a rotating surface. The sorting device 116 may rotate the imaging platform 112 toward the appropriate sorting chamber 118A, 118B to release the insect into the chamber 118A, 118B.

Figure 4:
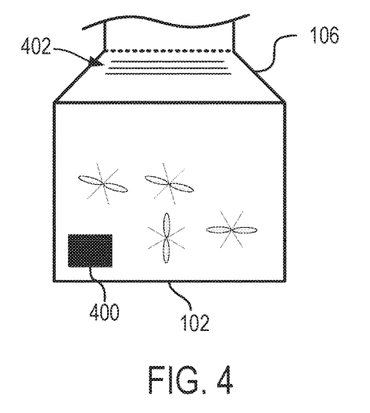
FIG. 4 is a top cross-sectional view of an insect chamber of the insect singulator system of FIG. 1 including an irritant according to some aspects of the present disclosure.
Figure 5:
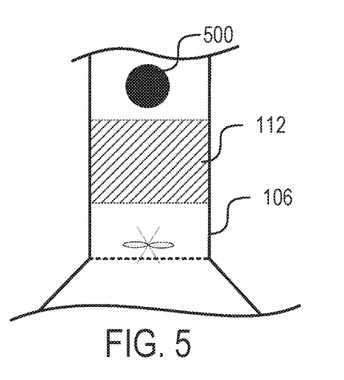
FIG. 5 is a top cross-sectional view of the singulation chamber of FIG. 2A including a lure according to some aspects of the present disclosure.
Figure 6:
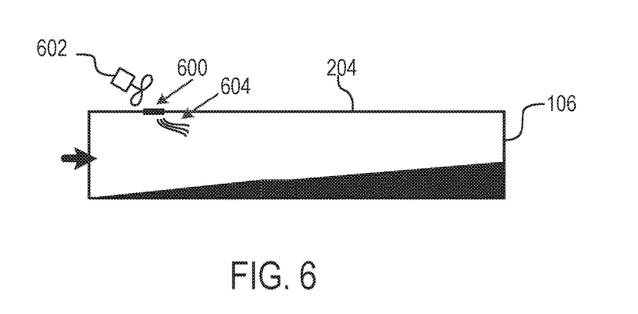
FIG. 6 is a side cross-sectional view of a singulation chamber including a draft opening according to some aspects of the present disclosure.

FIGS. 4-6 illustrate examples of additional features that may be included in the insect chamber 102 or the singulation chamber 106 of the insect singulator system 100 of FIG. 1. FIG. 4 shows the insect chamber 102 including an irritant 400. The irritant 400 may include any object or substance to repel mosquitoes (e.g., encourage the mosquitoes 104 within the insect chamber 102 to move away from the irritant 400). In some aspects, the irritant 400 is positioned in a location that encourages the mosquitoes to move away from the irritant 400 toward the opening 110. For example, the irritant 400 may be placed in a corner of the insect chamber 102 that is opposite a corner in which the opening 110 is located.

Similarly, the irritant 400 may be placed on a floor surface of the insect chamber 102 when the opening 110 is positioned on a top or ceiling surface of the insect chamber 102. Non-limiting examples of an irritant 400 include one or more drops of eucalyptus, imitation vanilla extract, apple cider vinegar, a deionizer, a vibrating device, and an electric grid.

The insect chamber 102 also includes a ridged surface 402 positioned proximate to the opening 110. The ridged surface includes one or more ridges, protrusions, or indentations in the surface of the insect chamber 102. The mosquitoes 104 have a tendency to cling to non-linear or non-smooth surfaces. By providing a ridged surface 402 proximate to the opening 110, the mosquitoes are encouraged to hang onto the ridges of the ridged surface 402 and crawl through the opening 110 into the singulation chamber 106. In some aspects, a smooth surface (e.g., a plastic cylinder) is positioned below the ridged surface 402 to encourage the mosquitoes to fly past the smooth surface to reach the ridges.

In FIG. 5, a lure 500 is positioned in the singulation chamber 106 to encourage the mosquitoes to navigate toward through the opening 110 and toward the imaging platform 112. The lure 500 may include an object or substance that attracts the mosquitoes 104. Non-limiting examples of a lure 500 include a light, a heat source, carbon dioxide, and drops of sugar water, honey, or another sweet-fragranced substance.

In FIG. 6, the singulation chamber 106 includes an opening 600 on a surface (e.g., the top 204). The opening 600 may be small, such as a slit, to prevent the mosquitoes 104 from navigating through the opening 600. A fan 602 or other draft-generating means is positioned proximate to the opening 600. When operating, the fan 602 generates a draft 604 that traverses the opening 600 and blows in the desired direction through the singulation chamber 106. The mosquitoes have a tendency to crawl toward an air draft, thus are encouraged to crawl in the direction of the draft 604 toward the imaging platform 112 of FIG. 1.

Although FIGS. 4-6 include specific combinations of features that may be incorporated into the insect singulator system 100 to encourage the mosquitoes 104 to navigate themselves in a desired direction for sorting, any combination of features discussed herein may be included in the insect singulator system 100 without departing from the scope of the present disclosure. For example, the lure 500 of FIG. 5 and the draft 604 of FIG. 6 may be combined such that the draft distributes a scent associated with the lure 500 over the opening 110 to encourage the mosquitoes to enter the singulation chamber 106. Similarly, although the features are shown in specific chambers or on specific surfaces of the insect singulator system 100, the features may be positioned in various locations without departing from the scope of the present disclosure.

Figure 7:
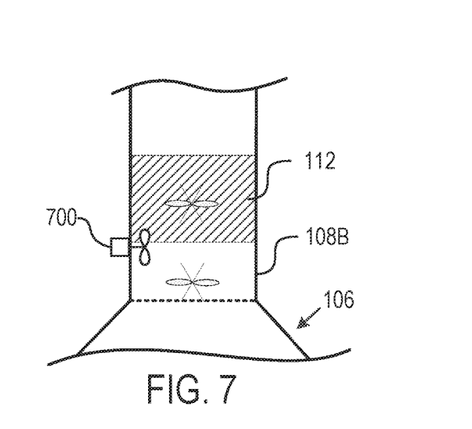
FIG. 7 is a top cross-sectional view of an insect chamber attached to an imaging platform and including an air jet according to some aspects of the present disclosure.
Figure 8A:
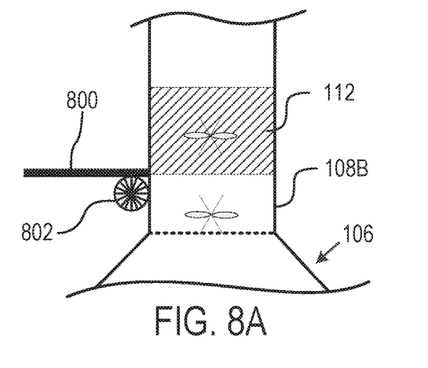
FIG. 8A is a top cross-sectional view of a shutter device in an open position between an insect chamber and an imaging platform according to some aspects of the present disclosure.
Figure 8B:
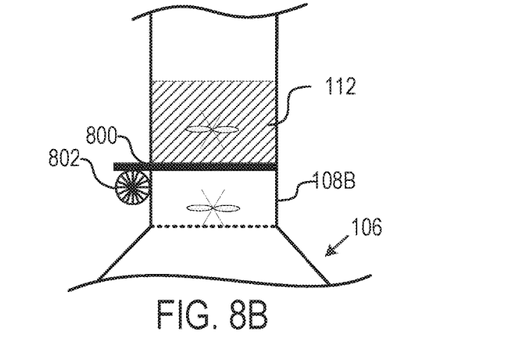
FIG. 8B is a top cross-sectional view of the shutter device of FIG. 8A in a closed position according to some aspects of the present disclosure.

FIGS. 7, 8A, and 8B illustrate examples of features that may be included in the singulation chamber 106 of the insect singulator system 100 of FIG. 1 to prevent multiple mosquitoes 104 from entering the imaging platform 112 at the same time. FIG. 7 includes an air jet 700 positioned proximate to the opposing end 108B of the singulation chamber 106. In some examples, the air jet 700 is positioned between the opposing end 108B and the imaging platform 112 as shown in FIG. 7. In other aspects, the air jet 700 is positioned within the singulation chamber 106 or within the imaging platform 112. The air jet may include a fan, similar to fan 602 of FIG. 6, or other air-generating means to cause a puff of air to blow into the chamber 106 in the direction of the receiving end 108. The puff of air may blow back all but a single mosquito 104 entering the imaging platform 112 at the same time to allow only one mosquito 104 to be analyzed at a time. In some aspects, the air jet 700 is communicatively coupled to a sensor that senses when multiple mosquitoes 104 are entering the imaging platform 112. In additional aspects, the air jet 700 is communicatively coupled to a processing device that transmits a control signal to activate the air puff in response to a signal received from the signal indicating multiple mosquitoes 104 in the imaging platform 112. In further aspects, one or both of the sensor and processing device functions may be implemented by the imaging device 114 or characteristic analysis system 115.

FIGS. 8A and 8B show a shutter device 800 positioned between the singulation chamber 106 and the imaging platform 112. The shutter device 800 may include any material having sufficient rigidity to prevent a mosquito 104 from entering the imaging platform 112 from the singulation chamber 106. Non-limiting examples of the shutter device 800 material include wood and plastic. The shutter device 800 may be controlled by an actuation mechanism 802. The actuation mechanism 802 may include a gear, piston, or other means for moving the shutter device 800 between an open position and a closed position. In the open position, the shutter device 800 may be positioned away from an opening between the singulation chamber 106 and the imaging platform 112. In the closed position, the shutter device 800 may be positioned between the singulation chamber 106 and the imaging platform 112 to prevent mosquitoes 104 from entering the imaging platform 112. In some aspects, the actuation mechanism 802 is communicatively coupled to a sensor that senses when a mosquito 104 has entered the imaging platform 112. In additional aspects, the actuation mechanism 802 is communicatively coupled to a processing device that transmits a control signal to activate the actuation mechanism 802 in response to a signal received from the sensor indicating a mosquito 104 in the imaging platform 112. In further aspects, one or both of the sensor and processing device functions may be implemented by the imaging device 114 or characteristic analysis system 115.

Figure 9:
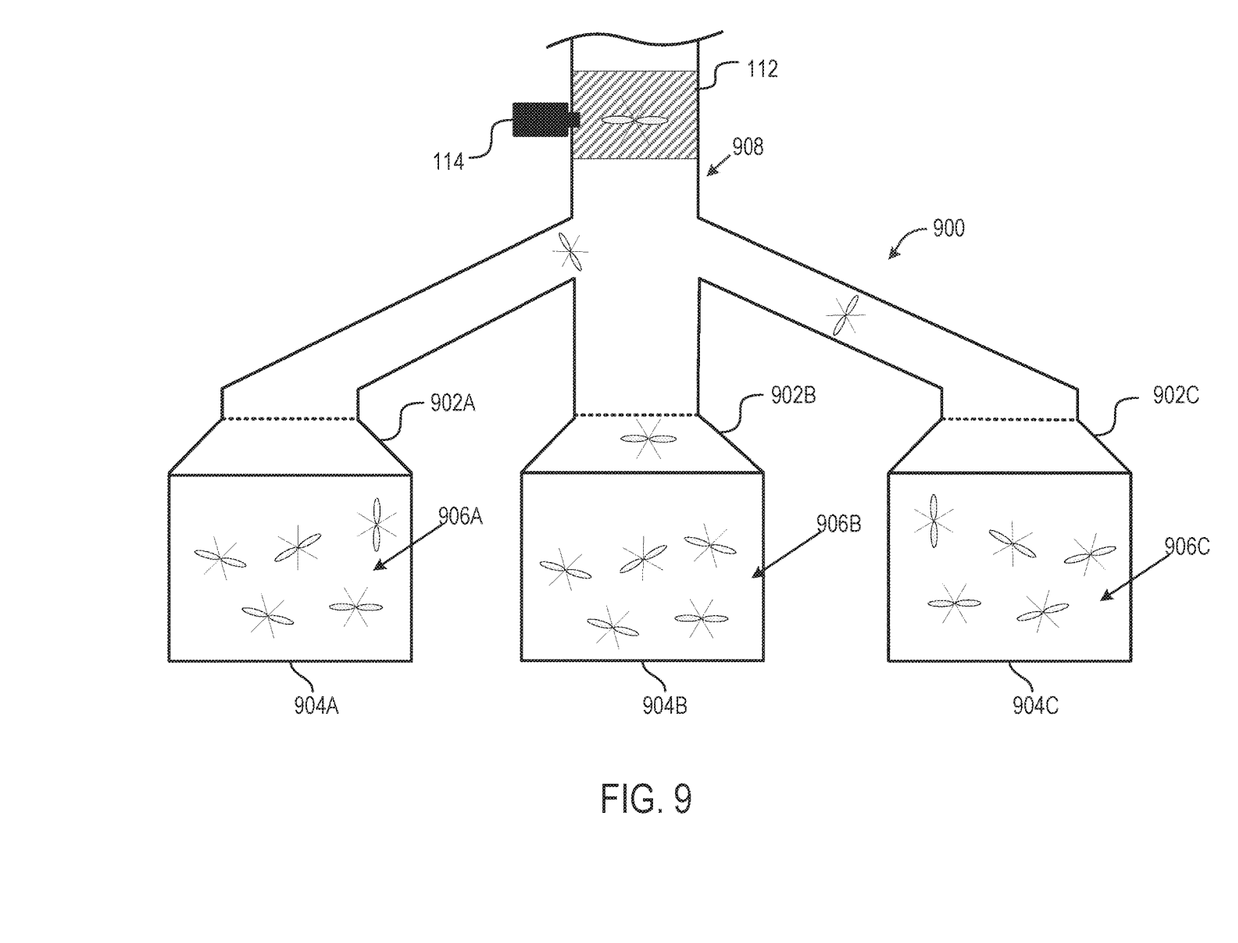
FIG. 9 is a top cross-sectional view of an insect singulator system including multiple singulation chambers according to some aspects of the present disclosure.

FIG. 9 shows a singulation chamber 900 that may be used in the insect singulator system 100 of FIG. 1 in place of the singulation chamber 106 of FIG. 1. In FIG. 9, the imaging platform 112 is connected to a singulation chamber 900 that includes multiple receiving ends 902A, 902B, 902C. Each of the receiving ends 902A, 902B, 902C is connected to a separate insect chamber 904A, 904B, 904C that include separate groups of mosquitoes 906A, 906B, 906C. A common opposing end 908 of the singulation chamber 900 opposite the receiving ends 902A, 902B, 902C is connected to the imaging platform 112. The singulation chamber 900 may operate similar to the singulation chamber 106 of FIG. 1 described herein, but may accelerate the sorting process by increasing the rate at which the mosquitoes reach the imaging platform 112 from the insect chambers 904A, 904B, 904C. For example, performing the process 300 of FIG. 3 using the singulator of FIG. 1 may result in a mosquito reaching the imaging platform 112 every 15 minutes. The singulation chamber 900 may accelerate the process 300 by a multiple of the number of insect chambers 904A, 904B, 904C connected to the imaging platform 112 using the singulation chamber 900 (e.g., three times as fast where a mosquito reaches the imaging platform 112 every 5 minutes). Although the singulation chamber 900 is shown as including three receiving ends 902A, 902B, 902C, the singulation chamber 900 may include any number of receiving ends connected to any number of insect chambers without departing from the scope of the present disclosure.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

What is claimed is:

1. An apparatus, comprising:
a chamber defining a volume having a receiving end and an opposing end,
wherein the receiving end is coupled to an insect chamber for a plurality of ambulatory insects and defines an opening to receive the plurality of ambulatory insects from the insect chamber, and
wherein a surface of the chamber is ramped to provide a pathway between the receiving end and the opposing end such that the opposing end is elevated with respect to the first end via the ramped surface, a portion of the pathway toward the opposing end having a width sized to accommodate a single-file line of the plurality of ambulatory insects traversing the ramped surface.

2. The apparatus of claim 1, wherein the surface includes ridges positioned in the pathway.

3. The apparatus of claim 1, wherein the ramped surface includes at least two ramps positioned on the ramped surface to orient the plurality of ambulatory insects headfirst toward the opposing end.

4. The apparatus of claim 1, wherein the portion of the pathway toward the opposing end further has a height sized to prevent an insect of the plurality of ambulatory insects from flying within the chamber.

5. The apparatus of claim 1, wherein the chamber includes (i) side walls defining the pathway between the receiving end and the opposing end and (ii) a top section enclosing the pathway, the side walls and the top section having smooth surfaces.

6. The apparatus of claim 5, wherein the top section comprises a glass material.

7. The apparatus of claim 5, wherein the side walls comprise a glass material.

8. The apparatus of claim 5, wherein the top section comprises a translucent material to permit light into the receiving end or the pathway.

9. The apparatus of claim 1, wherein the chamber includes a top section defining a ceiling of the pathway, the top section including a second opening to permit a draft of air into the pathway in a direction toward the opposing end.

10. The apparatus of claim 1, wherein the volume of the chamber has a second receiving end coupled to a second insect chamber and defines a second opening to receive a second plurality of ambulatory insects from the second insect chamber.

11. The apparatus of claim 1, wherein the opposing end is coupled to an imaging platform for sorting each insect of the plurality of ambulatory insects, wherein an air jet is positioned proximate to the opposing end to prevent multiple insects of the plurality of ambulatory insects from entering the imaging platform at the same time.

12. The apparatus of claim 1, wherein the opposing end is coupled to an imaging platform for sorting each insect of the plurality of ambulatory insects, wherein a shutter device is positioned between the opposing end and the imaging platform to prevent multiple insects of the plurality of ambulatory insects from entering the imaging platform at the same time.

13. A system, comprising:
an insect chamber including a plurality of ambulatory insects;
an imaging platform positioned proximate to an imaging device configured to generate a visual medium including an insect of the plurality of ambulatory insects, the visual medium usable to sort the insect into a new chamber based on a characteristic of the insect captured in the visual medium; and
a singulation chamber defining a volume having a receiving end coupled to the insect chamber and an opposing end coupled to the imaging platform, the receiving end defining an opening to receive the plurality of ambulatory insects,
wherein a surface of the singulation chamber is shaped to provide a pathway between the insect chamber and the imaging platform, a portion of the pathway toward the imaging platform having a width sized to accommodate a single-file line of the plurality of ambulatory insects traversing the surface.

14. The system of claim 13, wherein the plurality of ambulatory insects includes a plurality of mosquitoes.

15. The system of claim 13, wherein the insect chamber includes ridges formed proximate to the opening.

16. The system of claim 15, wherein the ridges are formed on a top surface of the insect chamber, wherein a bottom surface of the insect chamber below the ridges comprises a smooth surface.

17. The system of claim 13, wherein the surface includes one or more ramps positioned on the surface to orient the plurality of ambulatory insects headfirst toward the imaging platform.

18. The system of claim 13, further comprising a lure positioned in the pathway to attract the plurality of ambulatory insects to voluntarily navigate from the opening to the imaging platform.

19. The system of claim 13, further comprising an irritant positioned in the insect chamber to repel the plurality of ambulatory insects toward the opening.

20. The system of claim 13, wherein the singulation chamber includes a top section, defining a ceiling of the pathway, wherein a second opening is formed in the top section to allow an air draft to flow into the singulation chamber in a direction of the imaging platform.

21. The system of claim 13, wherein the volume of the singulation chamber has a second receiving end coupled to a second insect chamber and defines a second opening to receive a second plurality of ambulatory insects from the second insect chamber.

22. The system of claim 13, wherein an air jet is positioned proximate to the opposing end to prevent multiple insects of the plurality of ambulatory insects from entering the imaging platform at the same time.

23. The apparatus of claim 13, wherein a shutter device is positioned between the opposing end and the imaging platform to prevent multiple insects of the plurality of ambulatory insects from entering the imaging platform at the same time.

24. A method, comprising:
providing a singulation chamber, the singulation chamber defining a volume having a receiving end coupled to the insect chamber and an opposing end, the receiving end defining an opening, wherein a surface of the singulation chamber defines a pathway between the receiving end and the opposing end, a portion of the pathway toward the opposing end having a width sized to accommodate a single-file line of a plurality of ambulatory insects traversing the surface;
positioning an insect chamber including the plurality of ambulatory insects at the receiving end of the singulation chamber to allow the plurality of ambulatory insects to enter the singulation chamber from the insect chamber through the opening; and
receiving an insect of the plurality of ambulatory insects at the opposing end, the insect having voluntarily navigated the pathway in a single-file line, the single-file line comprising a subset of the plurality of ambulatory insects.

25. The method of claim 24, further comprising:
generating a visual medium associated with the insect positioned on an imaging platform coupled to the opposing end of the singulation chamber;
identifying a characteristic of the insect based on the visual medium; and
sorting the insect in a chamber of a plurality of sorting chambers based on the presence or absence of the characteristic.

26. The method of claim 24, further comprising positioning a lure in the singulation chamber to attract the insect to voluntarily navigate toward an imaging platform positioned proximate to the opposing end.

27. The method of claim 24, further comprising positioning an irritant in the insect chamber to repel the plurality of ambulatory insects away from the irritant and toward the opening.

28. The method of claim 24, further comprising positioning a fan proximate to a second opening in the singulation chamber to cause an air draft to traverse at least a portion of the singulation chamber in a direction of the opposing end of the singulation chamber.

29. The method of claim 24, further comprising positioning a light source proximate to a top section of the singulation chamber, the top section comprising a translucent material to allow light signals from the light source to enter the singulation chamber.

30. The method of claim 24, wherein the characteristic includes a physical characteristic consistent with a specific gender of the plurality of ambulatory insects.

31. The method of claim 24, wherein the characteristic includes a behavioral characteristic consistent with a predetermined level of fitness of the plurality of ambulatory insects.

32. An apparatus, comprising:
a chamber defining a volume having a plurality of receiving ends and a common opposing end,
wherein the plurality of receiving ends are couplable to a plurality of insect chambers, each insect chamber of the plurality of insect chambers including a corresponding set of ambulatory insects, each receiving end of the plurality of receiving ends defining a respective opening to receive the corresponding set of ambulatory insects, and
wherein a surface of the chamber defines a plurality of pathways between the plurality of receiving ends and the common opposing end, portions of each pathway of the plurality of pathways toward the common opposing end having width size to accommodate a respective single-file line of the corresponding set of ambulatory insects traversing each pathway.

33. The apparatus of claim 32, wherein the chamber includes a plurality of side walls defining the plurality of pathways, wherein each respective opening defined by the plurality of receiving ends is formed proximate to a side wall of the plurality of side walls.

34. The apparatus of claim 32, wherein the chamber includes a plurality of side walls defining the plurality of pathways and a top section enclosing the plurality of pathways, the plurality of side walls and the top section comprising smooth surfaces.

35. The apparatus of claim 32, wherein the common opposing end is coupled to an imaging platform for sorting insects traversing the pathway from the plurality of insect chambers, wherein an air jet is positioned proximate to the common opposing end to prevent multiple insects from the plurality of insect chambers from entering the imaging platform at the same time.

36. The apparatus of claim 32, wherein the common opposing end is coupled to an imaging platform for sorting insects traversing the pathway from the plurality of insect chambers, wherein a shutter device is positioned between the opposing end and the imaging platform to prevent multiple insects from the plurality of insect chambers from entering the imaging platform at the same time.

* * * * *